(12) United States Patent
Reisinger (10) Patent No.: US 9,509,272 B2
(45) Date of Patent: *Nov. 29, 2016

(54) CERAMIC BUSHING WITH FILTER

(71) Applicant: Heraeus Precious Metals GmbH & Co. KG, Hanau (DE)

(72) Inventor: Andreas Reisinger, Alzenau (DE)

(73) Assignee: Heraeus Deutschland GmbH & Co. KG, Hanau (DE)

( * ) Notice: Subject to any disclaimer, the term of this patent is extended or adjusted under 35 U.S.C. 154(b) by 139 days.

This patent is subject to a terminal disclaimer.

(21) Appl. No.: 14/474,569

(22) Filed: Sep. 2, 2014

(65) Prior Publication Data
US 2014/0368298 A1  Dec. 18, 2014

Related U.S. Application Data

(63) Continuation of application No. 13/361,383, filed on Jan. 30, 2012, now Pat. No. 8,825,162.

(60) Provisional application No. 61/438,047, filed on Jan. 31, 2011.

(30) Foreign Application Priority Data

Jan. 31, 2011 (DE) .................. 10 2011 009 855

(51) Int. Cl.
*H03H 7/01* (2006.01)
*H01R 43/16* (2006.01)
(Continued)

(52) U.S. Cl.
CPC .......... *H03H 7/0138* (2013.01); *A61N 1/3754* (2013.01); *H01G 11/30* (2013.01);
(Continued)

(58) Field of Classification Search
CPC .... H03H 7/0138; H03H 9/54; H01P 11/007; H01R 43/16
USPC ........................ 333/185, 186; 29/601; 174/18
See application file for complete search history.

(56) References Cited

U.S. PATENT DOCUMENTS 3,025,441 A  3/1962 West
3,063,144 A  11/1962 Palmour, III
(Continued)

FOREIGN PATENT DOCUMENTS

CN   1452232   10/2003
DE   69729719   7/2005
(Continued)

OTHER PUBLICATIONS

Notice of Allowance for U.S. Appl. No. 13/361,398 mailed Jul. 25, 2014 (11 pages).
(Continued)

*Primary Examiner* — Timothy Thompson
*Assistant Examiner* — Charles Pizzuto
(74) *Attorney, Agent, or Firm* — Dicke, Billig & Czaja, PLLC (57) ABSTRACT

On aspect relates to an electrical bushing for use in a housing of an implantable medical device. The bushing includes at least one electrically insulating base body and at least one electrical conducting element. The conducting element is set up to establish, through the base body, at least one electrically conductive connection between an internal space of the housing and an external space. The at least one conducting element comprises at least one cermet such that the conducting element is hermetically sealed with respect to the base body. The bushing includes an electrical filter structure. The at least one conducting element provides at least a one conducting section of the filter structure and the base body provides at least one dielectric section of the filter.

16 Claims, 2 Drawing Sheets

(51) Int. Cl.
 *H03H 9/54*     (2006.01)
 *H01P 11/00*    (2006.01)
 *A61N 1/375*    (2006.01)
 *H01G 11/30*    (2013.01)

(52) U.S. Cl.
 CPC ............ *H01P 11/007* (2013.01); *H01R 43/16* (2013.01); *H03H 9/54* (2013.01); *Y02E 60/13* (2013.01); *Y10T 29/49018* (2015.01); *Y10T 29/49204* (2015.01)

(56) References Cited

U.S. PATENT DOCUMENTS

| | | | |
|---|---|---|---|
| 3,646,405 A | 2/1972 | Wallis et al. | |
| 3,979,187 A | 9/1976 | Scherer | |
| 4,152,540 A | 5/1979 | Duncan et al. | |
| 4,159,075 A | 6/1979 | Ljung et al. | |
| 4,217,137 A | 8/1980 | Kraska et al. | |
| 4,225,262 A | 9/1980 | Koop et al. | |
| 4,315,054 A | 2/1982 | Sack et al. | |
| 4,354,964 A | 10/1982 | Hing et al. | |
| 4,488,673 A | 12/1984 | Hopper, Jr. | |
| 4,602,956 A | 7/1986 | Partlow et al. | |
| 4,678,868 A | 7/1987 | Kraska et al. | |
| 4,991,582 A | 2/1991 | Byers et al. | |
| 5,043,535 A | 8/1991 | Lin | |
| 5,515,604 A | 5/1996 | Horine et al. | |
| 5,601,638 A | 2/1997 | Fukuda et al. | |
| 5,735,884 A | 4/1998 | Thompson et al. | |
| 5,738,270 A | 4/1998 | Malmgren | |
| 5,769,874 A | 6/1998 | Dahlberg | |
| 5,796,019 A | 8/1998 | Lupton et al. | |
| 5,861,714 A | 1/1999 | Wei et al. | |
| 5,870,272 A | 2/1999 | Seifried et al. | |
| 6,093,476 A | 7/2000 | Horiuchi et al. | |
| 6,414,835 B1 | 7/2002 | Wolf et al. | |
| 6,643,903 B2 | 11/2003 | Stevenson et al. | |
| 6,660,116 B2 * | 12/2003 | Wolf .................. | A61N 1/3754 156/89.12 |
| 6,841,731 B1 | 1/2005 | Zanello | |
| 6,999,818 B2 | 2/2006 | Stevenson et al. | |
| 7,035,076 B1 | 4/2006 | Stevenson | |
| 7,038,900 B2 | 5/2006 | Stevenson et al. | |
| 7,136,273 B2 | 11/2006 | Stevenson et al. | |
| 7,145,076 B2 | 12/2006 | Knappen et al. | |
| 7,174,219 B2 | 2/2007 | Wahlstrand et al. | |
| 7,174,223 B2 | 2/2007 | Dalton et al. | |
| 7,211,103 B2 | 5/2007 | Greenberg et al. | |
| 7,260,434 B1 | 8/2007 | Lim et al. | |
| 7,274,963 B2 | 9/2007 | Spadgenske | |
| 7,341,802 B1 | 3/2008 | Ota et al. | |
| 7,437,817 B2 | 10/2008 | Zhang et al. | |
| 7,480,988 B2 | 1/2009 | Ok et al. | |
| 7,502,217 B2 | 3/2009 | Zhao et al. | |
| 7,561,917 B2 | 7/2009 | Wegrzyn, III et al. | |
| 7,564,674 B2 | 7/2009 | Frysz et al. | |
| 7,630,768 B1 | 12/2009 | Coffed et al. | |
| 7,706,124 B2 | 4/2010 | Zhao et al. | |
| 7,720,538 B2 | 5/2010 | Janzig et al. | |
| 7,736,191 B1 | 6/2010 | Sochor | |
| 7,742,817 B2 | 6/2010 | Malinowski et al. | |
| 7,747,321 B2 | 6/2010 | Fischbach et al. | |
| 7,761,165 B1 | 7/2010 | He et al. | |
| 7,765,005 B2 | 7/2010 | Stevenson | |
| 7,794,256 B1 | 9/2010 | Sochor | |
| 7,901,761 B1 | 3/2011 | Jiang et al. | |
| 7,930,032 B2 | 4/2011 | Teske et al. | |
| 7,970,474 B2 | 6/2011 | Starke | |
| 7,989,080 B2 | 8/2011 | Greenberg et al. | |
| 8,000,804 B1 * | 8/2011 | Wessendorf ......... | A61N 1/0543 607/115 |
| 8,065,009 B2 | 11/2011 | Biggs | |
| 8,131,369 B2 | 3/2012 | Taylor et al. | |
| 8,131,376 B1 | 3/2012 | Faraji et al. | |
| 8,163,397 B2 | 4/2012 | Ok et al. | |
| 8,179,658 B2 * | 5/2012 | Brendel ............... | A61N 1/3754 333/183 |
| 8,288,654 B2 | 10/2012 | Taylor et al. | |
| 8,289,105 B2 * | 10/2012 | Chereson ................ | H01C 7/10 333/182 |
| 8,326,425 B2 | 12/2012 | Sprain et al. | |
| 8,346,362 B2 | 1/2013 | Kinney et al. | |
| 8,355,785 B1 | 1/2013 | Hammond et al. | |
| 8,378,239 B2 | 2/2013 | Lakner et al. | |
| 8,391,983 B2 | 3/2013 | Lim | |
| 8,494,635 B2 | 7/2013 | Troetzschel et al. | |
| 8,497,435 B2 | 7/2013 | Nagata et al. | |
| 8,528,201 B2 | 9/2013 | Troetzschel et al. | |
| 8,538,530 B1 | 9/2013 | Orinski | |
| 8,552,311 B2 | 10/2013 | Koester et al. | |
| 8,626,310 B2 | 1/2014 | Barror et al. | |
| 8,656,736 B2 | 2/2014 | Terao | |
| 8,659,870 B2 | 2/2014 | Brendel et al. | |
| 8,742,268 B2 | 6/2014 | Reisinger et al. | |
| 8,825,162 B2 | 9/2014 | Reisinger | |
| 8,894,914 B2 | 11/2014 | Pavlovic | |
| 9,032,614 B2 | 5/2015 | Specht | |
| 9,040,819 B2 | 5/2015 | Kempf et al. | |
| 9,048,608 B2 | 6/2015 | Pavlovic | |
| 9,088,093 B2 | 7/2015 | Reisinger et al. | |
| 9,126,053 B2 | 9/2015 | Kempf et al. | |
| 9,306,318 B2 | 4/2016 | Reisinger | |
| 2001/0013756 A1 | 8/2001 | Mori et al. | |
| 2004/0116976 A1 | 6/2004 | Spadgenske | |
| 2004/0128016 A1 | 7/2004 | Stewart | |
| 2006/0247714 A1 | 11/2006 | Taylor et al. | |
| 2006/0259093 A1 | 11/2006 | Stevenson et al. | |
| 2007/0183118 A1 | 8/2007 | Fu et al. | |
| 2008/0060834 A1 | 3/2008 | Eck et al. | |
| 2008/0060844 A1 | 3/2008 | Teske et al. | |
| 2008/0071313 A1 | 3/2008 | Stevenson et al. | |
| 2008/0119906 A1 | 5/2008 | Starke | |
| 2008/0203917 A1 | 8/2008 | Maya | |
| 2008/0269831 A1 | 10/2008 | Erickson | |
| 2008/0314502 A1 | 12/2008 | Ok et al. | |
| 2009/0192578 A1 | 7/2009 | Biggs | |
| 2009/0281586 A1 | 11/2009 | Lim | |
| 2010/0023086 A1 | 1/2010 | Lim | |
| 2010/0109966 A1 | 5/2010 | Mateychuk et al. | |
| 2010/0258342 A1 | 10/2010 | Parker | |
| 2011/0034965 A1 | 2/2011 | Troetzschel et al. | |
| 2011/0034966 A1 | 2/2011 | Troetzschel et al. | |
| 2011/0048770 A1 | 3/2011 | Reiterer et al. | |
| 2011/0186349 A1 | 8/2011 | Troetzschel et al. | |
| 2012/0127627 A1 | 5/2012 | Brendel et al. | |
| 2012/0193117 A1 | 8/2012 | Specht et al. | |
| 2012/0193118 A1 | 8/2012 | Kempf et al. | |
| 2012/0193119 A1 | 8/2012 | Kempf et al. | |
| 2012/0193125 A1 | 8/2012 | Pavlovic et al. | |
| 2012/0193141 A1 | 8/2012 | Reisinger et al. | |
| 2012/0194981 A1 | 8/2012 | Kempf et al. | |
| 2012/0197326 A1 | 8/2012 | Pavlovic | |
| 2012/0197327 A1 | 8/2012 | Specht | |
| 2012/0197335 A1 | 8/2012 | Reisinger | |
| 2012/0197368 A1 * | 8/2012 | Reisinger ............. | A61N 1/3754 607/116 |
| 2012/0200011 A1 | 8/2012 | Pavlovic | |
| 2012/0203294 A1 | 8/2012 | Troetzschel | |
| 2014/0262494 A1 | 9/2014 | Reisinger et al. | |
| 2015/0122875 A1 | 5/2015 | Pavlovic et al. | |
| 2015/0270025 A1 | 9/2015 | Specht et al. | |

FOREIGN PATENT DOCUMENTS

| | | |
|---|---|---|
| DE | 102006054249 | 5/2008 |
| DE | 102008021064 | 10/2009 |
| DE | 102009035971 | 2/2011 |
| DE | 102009035972 | 4/2011 |
| DE | 102010006837 | 8/2011 |
| DE | 102010006838 | 8/2011 |
| DE | 102010006689 | 9/2011 |
| DE | 102010006690 | 9/2011 |
| EP | 0877400 | 11/1998 |
| EP | 1685874 | 8/2006 |

(56) References Cited

FOREIGN PATENT DOCUMENTS

| EP | 1754511 | 2/2007 |
|---|---|---|
| WO | 03073450 | 9/2003 |
| WO | 2004110555 | 12/2004 |
| WO | 2008103166 | 8/2008 |
| WO | 2010091435 | 8/2010 |

OTHER PUBLICATIONS

Final Office Action for U.S. Appl. No. 13/361,404 mailed Oct. 9, 2014 (12 pages).
Office Action for U.S. Appl. No. 13/361,411 mailed Aug. 1, 2014 (18 pages).
Office Action for U.S. Appl. No. 13/361,322 mailed Feb. 4, 2015 (19 pages).
Notice of Allowance for U.S. Appl. No. 13/361,348 mailed Jan. 22, 2015 (9 pages).
Notice of Allowance for U.S. Appl. No. 13/361,404 mailed Jan. 28, 2015 (6 pages).
Notice of Allowance for U.S. Appl. No. 13/361,411 mailed Jan. 20, 2015 (8 pages).
Office Action for U.S. Appl. No. 13/361,388 mailed Feb. 9, 2015 (29 pages).
Hussain, et al., "Electrical conductivity of an insulator matrix (alumina) and conductor particle (molybdenum) composites", Journal of the European Ceramic Society, vol. 23, Issue 2, Feb. 2003, pp. 315-321.
Office Action for U.S. Appl. No. 13/361,340 mailed Mar. 12, 2015 (23 pages).
Notice of Allowance for U.S. Appl. No. 14/293,596 mailed Mar. 17, 2015 (28 pages).
Notice of Allowance for U.S. Appl. No. 13/361,370 mailed May 1, 2015 (17 pages).
Office Action for U.S. Appl. No. 13/361,374 mailed May 18, 2015 (12 pages).
Final Office Action for U.S. Appl. No. 13/361,322 mailed Aug. 24, 2015 (21 pages).
Restriction Requirement for U.S. Appl. No. 14/729,560 mailed Dec. 22, 2015 (6 pages).
Restriction Requirement for U.S. Appl. No. 14/729,560 mailed Feb. 22, 2016 (7 pages).
Final Office Action for U.S. Appl. No. 13/361,340 mailed Nov. 24, 2015 (27 pages).
Advisory Action for U.S. Appl. No. 13/361,340 mailed Feb. 22, 2016 (4 pages).
Notice of Allowance for U.S. Appl. No. 13/361,374 mailed Dec. 3, 2015 (21 pages).
Corrected Notice of Allowability for U.S. Appl. No. 13/361,374 mailed Feb. 11, 2016 (7 pages).
Final Office Action for U.S. Appl. No. 13/361,388 mailed Sep. 11, 2015 (28 pages).
Office Action for U.S. Appl. No. 14/593,637 mailed May 26, 2016 (37 pages).
Restriction Requirement for U.S. Appl. No. 13/361,322 mailed Nov. 14, 2013 (7 pages).
Office Action for U.S. Appl. No. 13/361,322 mailed Feb. 19, 2014 (26 pages).
Office Action for U.S. Appl. No. 13/361,340 mailed Oct. 25, 2013 (20 pages).
Office Action for U.S. Appl. No. 13/361,340 mailed Apr. 29, 2014 (18 pages).
Restriction Requirement for U.S. Appl. No. 13/361,348 mailed Nov. 14, 2013 (7 pages).
Office Action for U.S. Appl. No. 13/361,348 mailed Feb. 19, 2014 (23 pages).
Office Action for U.S. Appl. No. 13/361,355 mailed date Aug. 7, 2013 (21 pages).
Notice of Allowance for U.S. Appl. No. 13/361,355 mailed Jan. 16, 2014 (18 pages).
Restriction Requirement for U.S. Appl. No. 13/361,362 mailed Nov. 14, 2013 (7 pages).
Office Action for U.S. Appl. No. 13/361,362 mailed Feb. 19, 2014 (19 pages).
Office Action for U.S. Appl. No. 13/361,370 mailed Oct. 29, 2013 (26 pages).
Office Action for U.S. Appl. No. 13/361,370 mailed May 14, 2014 (18 pages).
Restriction Requirement for U.S. Appl. No. 13/361,374 mailed Mar. 5, 2013 (6 pages).
Office Action for U.S. Appl. No. 13/361,374 mailed Oct. 4, 2013 (22 pages).
Office Action for U.S. Appl. No. 13/361,374 mailed May 1, 2014 (20 pages).
Restriction Requirement for U.S. Appl. No. 13/361,383 mailed Feb. 27, 2013 (6 pages).
Office Action for U.S. Appl. No. 13/361,383 mailed Nov. 13, 2013 (22 pages).
Notice of Allowance for U.S. Appl. No. 13/361,383 mailed Apr. 25, 2014 (18 pages).
Office Action for U.S. Appl. No. 13/361,388 mailed Feb. 11, 2014 (24 pages).
Office Action for U.S. Appl. No. 13/361,398 mailed Mar. 7, 2014 (26 pages).
Restriction Requirement for U.S. Appl. No. 13/361,404 mailed Apr. 8, 2013 (6 pages).
Restriction Requirement for U.S. Appl. No. 13/361,404 mailed Oct. 9, 2013 (5 pages).
Office Action for U.S. Appl. No. 13/361,404 mailed Feb. 27, 2014 (19 pages).
Restriction Requirement for U.S. Appl. No. 13/361,411 mailed Mar. 10, 2014 (7 pages).
Final Office Action for U.S. Appl. No. 13/361,322 mailed Sep. 9, 2014 (17 pages).
Final Office Action for U.S. Appl. No. 13/361,340 mailed Oct. 30, 2014 (21 pages).
Final Office Action for U.S. Appl. No. 13/361,348 mailed Sep. 9, 2014 (19 pages).
Final Office Action for U.S. Appl. No. 13/361,362 mailed Sep. 9, 2014 (19 pages).
Final Office Action for U.S. Appl. No. 13/361,370 mailed Nov. 5, 2014 (19 pages).
Final Office Action for U.S. Appl. No. 13/361,374 mailed Nov. 10, 2014 (19 pages).
Final Office Action for U.S. Appl. No. 13/361,388 mailed Jul. 31, 2014 (32 pages).

* cited by examiner

CERAMIC BUSHING WITH FILTER

CROSS-REFERENCE TO RELATED APPLICATIONS

This application is a continuation application of U.S. patent application Ser. No. 13/361,383 entitled "CERAMIC BUSHING WITH INDUCTIVE FILTER," having a filing date of Jan. 30, 2012, which claims the benefit of the filing date of U.S. Provisional Patent Application Ser. No. 61/438, 047, filed Jan. 31, 2011, entitled "CERAMIC BUSHING WITH INDUCTIVE FILTER," which claims priority to German Patent Application No. DE 10 2011 009 855.0, filed on Jan. 31, 2011, and all of which are incorporated herein by reference.

This patent application is also related to U.S. Pat. No. 8,678,668, issued Mar. 25, 2014, entitled "CERAMIC BUSHING FOR AN IMPLANTABLE MEDICAL DEVICE"; patent application Ser. No. 13/361,340 filed on Jan. 30, 2012, entitled "DIRECTLY APPLICABLE ELECTRICAL BUSHING"; patent application Ser. No. 13/361, 348 filed on Jan. 30, 2012, entitled "IMPLANTABLE DEVICE HAVING AN INTEGRATED CERAMIC BUSHING"; U.S. Pat. No. 8,742,268, issued Jun. 3, 2014, entitled "HEAD PART FOR AN IMPLANTABLE MEDICAL DEVICE"; patent application Ser. No. 13/361,362 filed on Jan. 30, 2012, entitled "CERMET-CONTAINING BUSHING FOR AN IMPLANTABLE MEDICAL DEVICE HAVING A CONNECTING LAYER"; patent application Ser. No. 13/361,370 filed on Jan. 30, 2012, entitled "ELECTRICAL BUSHING WITH CERMET-CONTAINING CONNECTING ELEMENT FOR AN ACTIVE IMPLANTABLE MEDICAL DEVICE"; patent application Ser. No. 13/361, 374 filed on Jan. 30, 2012, entitled "CERAMIC BUSHING WITH FILTER"; U.S. Pat. No. 8,747,639, issued Jun. 10, 2014, entitled "CERAMIC BUSHING HAVING HIGH CONDUCTIVITY CONDUCTING ELEMENTS"; patent application Ser. No. 13/361,398 filed on Jan. 30, 2012, entitled "METHOD FOR THE MANUFACTURE OF A CERMET-CONTAINING BUSHING"; patent application Ser. No. 13/361,404 filed on Jan. 30, 2012, entitled "METHOD FOR THE MANUFACTURE OF A CERMET-CONTAINING BUSHING FOR AN IMPLANTABLE MEDICAL DEVICE"; and patent application Ser. No. 13/361,411 filed on Jan. 30, 2012, entitled "CERMET-CONTAINING BUSHING WITH HOLDING ELEMENT FOR AN IMPLANTABLE MEDICAL DEVICE".

BACKGROUND

One aspect relates to an electrical bushing for use in a housing of an implantable medical device. Moreover, one aspect relates to a method for the manufacture of an electrical bushing for an implantable medical device.

The post-published document, DE 10 2009 035 972, discloses an electrical bushing for an implantable medical device having the features of the preamble of claim 1. Moreover, a use of at least one cermet-including conducting element in an electrical bushing for an implantable medical device and a method for the manufacture of an electrical bushing for an implantable medical device are disclosed.

A multitude of electrical bushings for various applications are known, examples including: U.S. Pat. Nos. 4,678,868, 7,564,674 B2, US 2008/0119906 A1, U.S. Pat. Nos. 7,145, 076 B2, 7,561,917, US 2007/0183118 A1, U.S. Pat. Nos. 7,260,434B1, 7,761,165, 7,742,817 B2, 7,736,191 B1, US 2006/0259093 A1, U.S. Pat. No. 7,274,963 B2, US 2004116976 A1, U.S. Pat. No. 7,794,256, US 2010/0023086 A1, U.S. Pat. Nos. 7,502,217 B2, 7,706,124 B2, 6,999,818 B2, EP 1754511 A2, U.S. Pat. No. 7,035,076, EP 1685874 A1, WO 03/073450 A1, U.S. Pat. Nos. 7,136,273, 7,765, 005, WO 2008/103166 A1, US 2008/0269831, U.S. Pat. No. 7,174,219 B2, WO 2004/110555 A1, U.S. Pat. No. 7,720, 538 B2, WO 2010/091435, US 2010/0258342 A1, US 2001/0013756 A1, U.S. Pat. No. 4,315,054, and EP 0877400.

DE 697 297 19 T2 describes an electrical bushing for an active implantable medical device—also called implantable device or therapeutic device. Electrical bushings of this type serve to establish an electrical connection between a hermetically sealed interior and an exterior of the therapeutic device. Known implantable therapeutic devices are cardiac pacemakers or defibrillators, which usually include a hermetically sealed metal housing which is provided with a connection body, also called header, on one of its sides. Said connection body includes a hollow space having at least one connection socket for connecting electrode leads. In this context, the connection socket includes electrical contacts in order to electrically connect the electrode leads to the control electronics on the interior of the housing of the implantable therapeutic device. Hermetic sealing with respect to a surrounding is an essential prerequisite of an electrical bushing of this type. Therefore, lead wires that are introduced into an electrically insulating base body—also called signal-transmission elements—through which the electrical signals are propagated, must be introduced into the base body such as to be free of gaps. In this context, it has proven to be challenging that the lead wires generally are made of a metal and are introduced into a ceramic base body. In order to ensure a durable connection between the two elements, the internal surface of a through-opening—also called openings—in the base body is metallized for attachment of the lead wires by soldering. However, the metallization in the through-opening has proven to be difficult to apply. Only expensive procedures ensure homogeneous metallization of the internal surface of the bore hole and thus a hermetically sealed connection of the lead wires to the base body by soldering. The soldering process itself requires additional components, such as solder rings. Moreover, the process of connecting the lead wires to the previously metallized insulators utilizing the solder rings is a process that is laborious and difficult to automate.

Printed publication U.S. Pat. No. 7,502,217 B2 describes a bushing for implantable devices, in which connection pins made of metal extend through an opening of an insulator. Aside from a filter capacitor, the bushing includes a coil as a separate component that is provided as a toroidal coil made of wire. A ring-shaped groove is provided in the bushing to accommodate the toroidal coil, which is embedded therein. The toroidal coil is connected to the filter capacitor and other wire connections of the bushing through solder connections. As a result, there are multiple connections concerning a multitude of components which have to be established through soldering. This not only renders the manufacturing method highly complex, but also makes the manufacture highly error-prone since the soldering steps concern different components, which each must be soldered in a certain way only. Due to the proximity of the various components to be soldered with respect to each other, especially in miniaturized versions, there is a risk that undesired solder connections may arise, even more so since previously established solder connections are partially melted again in each step of soldering. Moreover, an additional manufacturing step of introducing the groove in the bushing is required.

And lastly, the bushing body needs to be provided in the form of multiple parts in order to be able to take up the toroidal coil, whereby the multiple parts need to be connected to each other in an additional step.

For these and other reasons there is a need for the present invention.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Further measures and advantages of the invention are evident from the claims, the description provided hereinafter, and the drawings. The invention is illustrated through several exemplary embodiments in the drawings. In this context, equal or functionally equal or functionally corresponding elements are identified through the same reference numbers. The invention shall not be limited to the exemplary embodiments.

DETAILED DESCRIPTION

In the following Detailed Description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present invention. The following detailed description, therefore, is not to be taken in a limiting sense, and the scope of the present invention is defined by the appended claims.

It is to be understood that the features of the various exemplary embodiments described herein may be combined with each other, unless specifically noted otherwise.

One embodiment creates an electrical bushing for an implantable medical device, in which at least one of the disadvantages mentioned above is prevented at least in part. One embodiment provides a bushing having an inductive filter that can be manufactured easily, at high precision and low reject rates. Features and details that are described in the context of the electrical bushing or the implantable medical device shall also apply in relation to the method, and vice versa.

One embodiment enables, for example, the provision of an implantable device that is well-suited for MRI examinations. The inductor and/or the filter including it is capable of strongly attenuating the high frequency excitation pulse of a magnetic resonance imaging (MRI) apparatus as early as within the bushing, whereby the electronics unit of the device is protected from suffering electromagnetic damage.

One embodiment relates to an electrical bushing for use in a housing of an implantable medical device. The electrical bushing includes at least one electrically insulating base body and at least one electrical conducting element. The conducting element is set up to establish, through the base body, at least one electrically conductive connection between an internal space of the housing and an external space. The conducting element extends, for example, fully, through the base body, in one embodiment along a longitudinal axis of the base body. The bushing provides, for example, an upper side that is set up to be adjacent to the external space, and a lower side that is set up to be adjacent to the internal space. The conducting element extends at least between the lower side and the upper side. For electrical contacting, the conducting element borders directly on the space that is adjacent to the upper side, that is, on the external space, and borders directly on the space that is adjacent to the lower side, that is, on the internal space. The conducting element is hermetically sealed with respect to the base body. The at least one conducting element includes at least one cermet. The cermet is provided to be electrically conductive. The conducting element therefore forms a continuous electrically conductive structure in order to establish the electrically conductive connection. In one embodiment, the electrical connection is an ohmic connection with low resistance—in one embodiment, for a direct current signal—, that is, a resistance of, for example, no more than 10 Ohm, 1 Ohm, 100 mOhm, 10 mOhm or 1 mOhm. The specific conductivity of the conducting element, and/or of the electrically conductive structure provided by it, which connects the internal space to the external space, in one embodiment exceeds 1 S/m. The specific conductivity of the conducting element, and/or of the structure provided by it, is at least 1 S/m, at least 10 S/m, at least 100 S/m, at least 1000 S/m or at least $10^4$ S/m. In one embodiment, the specific conductivity is at least $10^5$ or $10^6$ and in one embodiment, at least $10^7$ S/m.

The base body is made from the insulating material either in part or fully. Said material corresponds to the at last one insulating material of the base body as described herein. The base body and the at least one conducting element are provided as a single part.

According to one embodiment, the electrical bushing includes an electrical filter structure. The at least one conducting element forms at least one conducting section of an inductor of the filter structure. Accordingly, the electrically conductive connection provides not only an ohmic connection, but also an inductor of the filter structure. Since the conducting element therefore forms not only the electrically conductive connection between the internal space and the external space of the housing and also forms a component of the filter structure, that is, the at least one inductor, the resulting manufacturing process is simplified and the degree of integration is increased.

The electrical filter structure forms an electrical filter. The electrical filter structure is connected to the electrically conductive connection which is established through the conducting element. An electrical filter structure shall be understood to be a network that has different impedances for different frequencies of a signal that is applied to the filter structure. The electrical filter structure is set up to provide different attenuations for different frequency components of a signal that is transmitted by the electrically conductive connection. The correlation of frequency and attenuation is also called frequency selectivity.

For example, the at least one conducting section is provided to have a longitudinal extension that deviates from a straight line. This makes the conducting section longer than the shortest distance between the points that are connected through the at least one conducting section. This allows the value of the inductor for the same volume to be increased as compared to the conducting section with a straight extension. The deviation of the longitudinal extension from a straight line can be provided through a kink or an arc shape or a combination thereof.

One embodiment further provides that the at least one conducting section provides at least a part of a turn of the inductor. The conducting section includes at least one arc shape or at least one kink. Accordingly, the coil does not necessarily have a circular or helical extension, but can comprise discrete changes of direction, which each are called kink. In one embodiment, the at least one conducting section includes one or more complete turns. Each turn includes a change of direction of the longitudinal extension of the conducting section by 360°. The direction of the conducting section along its extension can change in the form of discrete kinks or continuous curvatures in the form of an arc.

The at least one conducting section extends in two or three different directions of space. The at least one conducting section follows at least one repetitive triangular, trapezoidal or rectangular profile or follows a helix. A repetitive triangular profile includes kinks which in one embodiment form the same angle. The direction of kinking of subsequent kinks, in one embodiment of consecutive kinks, is opposite. The repetitive trapezoidal profile includes multiple kinks, whereby the kinks of a first group of two consecutive kinks have the same direction of kinking and the kinks of a directly subsequent second group of two kinks have a direction of kinking that is opposite from the direction of kinking of the kinks of the first group. The kinks of the second group have the same direction of kinking. The angle of the kinks of the trapezoidal profile can, for example, be 90°, which this case results in a rectangular profile. In one embodiment, the rectangular profile is provided by sections extension which extend either parallel or perpendicular to a straight line, for example, to a straight line that includes the points that are connected by the electrically conductive connection. The triangular, trapezoidal or rectangular profile in one embodiment extends in a plane and thus in two different directions in space. Alternatively, the conducting section extends spatially, that is, in three different directions in space. If the conducting section extends in three different directions in space, the angles given for the triangular, trapezoidal or rectangular profile shall refer to solid angles. Another embodiment provides that the at least one conducting section follows a helical profile. The conducting section thus extends in three different directions in space. The helix in one embodiment has a constant radius, but can just as well change its radius along the extension of the helix. Moreover, the helix can have a constant pitch along its longitudinal axis, whereby further embodiments provide the pitch to be positive and changing, though. Moreover, the at least one conducting section can follow a spiral profile, in one embodiment a spiral profile that extends in a plane.

A specific embodiment provides that the conducting section includes multiple kinks with an angle, whereby the angle formed by the kinks is equal and at least two angles between kinks differ in sign. Further embodiments provide the conducting section to include multiple kinks and the sub-sections between two consecutive kinks to be equal in length.

Further some embodiments provide that at least one further component, aside from the inductor, is provided by the base body and/or the conducting element. One embodiment thus provides that the conducting element provides at least one electrode surface of a capacitor or of an electromechanical resonator. The capacitor and/or the electromechanical resonator is/are provided by the filter structure.

Moreover, one embodiment can provide that a section of the electrically insulating base body forms a dielectric layer of the capacitor. Alternatively or in combination with this, one embodiment can provide that a section of the electrically insulating base body forms a piezoelectric body of the electromechanical resonator. According to this embodiment, a section of the electrically insulating base body forms a part of a component of the filter structure. The filter structure can therefore include multiple components that are provided by sections of the conducting element and/or by sections of the base body. A section of the conducting element can therefore provide an electrode surface or a conducting section of an inductor. A section of the conducting element forming an electrode surface differs from the conducting section of the conducting element forming the inductor. The filter structure can therefore include multiple components, for example, at least one inductor and at least one capacitor, that are provided by the conducting element and by the base body. Said components are provided, for example, by sections of the conducting element and by sections of the base body.

Further embodiments provide that the filter structure includes an additional frequency-selective component which is provided as an individual, physically independent component and is provided neither by the at least one conducting element, nor by the base body. Since the inductor provided according to in one embodiment, which is provided by the conducting element, itself is a frequency-selective component, further individual components of the filter structure shall be called additional frequency-selective component. Embodiments therefore provide that the filter structure includes an additional frequency-selective component. The conducting element forms at least one contact surface to which the additional frequency-selective component is connected. For example, the at least one connecting section forms the at least one contact surface. Moreover, a connector of the additional frequency-selective component is connected to the contact surface. The connection relates to an electrical connection for example. The additional frequency-selective component is provided as capacitor, as additional inductor, as electromechanical resonator or as integrated filter circuit. If the additional frequency-selective component is provided as capacitor, the capacitor can be provided as mica capacitor or ceramic capacitor or as foil-type capacitor, metallized paper capacitor, electrolyte capacitor or double-layer capacitor. If the additional frequency-selective component is provided as additional inductor, the additional inductor can be provided as coil with or without core. If the additional frequency-selective component is provided as electromechanical resonator, the resonator can be provided as crystal oscillator, SAW filter or BAW filter. SAW filters are also called surface wave filters with SAW meaning "surface acoustic wave". BAW filters are also called "bulk acoustic wave filters". An integrated filter circuit includes circuit elements that are integrated into a housing. The additional frequency-selective component forms an individual body and includes, if applicable, its own housing and in one embodiment connectors for electrical coupling. The frequency-selective component in one embodiment is an SMD component. For example, the type of design corresponds to a type of design defined by a standard, for example a JEDEC standard.

The additional frequency-selective component includes at least one connector. The connector is physically connected to the at least one contact surface through a solder connection or a press-fit. The connector forms an electrically conductive surface or is provided as an electrically conductive pin. A recess, in which the additional frequency-selective component is accommodated, can be provided in the electrical bushing according to one embodiment. In one embodiment, the recess is provided at a surface of the base body.

As a matter of principle, the filter structure can include one or more additional frequency-selective components. The additional frequency-selective components can be arranged on a surface of the electrical bushing, can be provided to be situated inside the bushing, for example, inside the base body, or can be provided to be situated in a recess that is provided on a surface of the base body and/or conducting section. Moreover, the electrical bushing can include a component bracket, in which an additional frequency-selective component is accommodated. The component bracket provides, aside from a mechanical bracket, at least one electrical contact.

In further refinements of embodiments, the filter structure includes the inductor formed by the conducting element as serial filter in the electrically conductive connection. The inductor provided by the conducting element is thus a serial filter inductor. Moreover, the filter structure can include at least one capacitor element in the form of a capacitor, whose at least one electrode surface is formed by the conducting element. Moreover, instead or in combination, the filter structure can include a capacitor element in the form of the capacitor provided as additional frequency-selective component. Said capacitor element and the inductor provided by the conducting element together form an LC anti-resonant circuit. The anti-resonant circuit thus provided is arranged in series in the electrically conductive connection.

The bushing according to one embodiment can be provided to have a filter structure, whereby the at least one conducting element includes, aside from the inductor of the filter structure that is provided by the conducting section of the conducting element, at least one electrically conductive surface of the filter structure, as is described in application "Ceramic bushing with filter", applicant: W. C. Heraeus GmbH, filing date: 31 Jan. 2011 under the internal file number P11392, to which reference shall be made herewith. For example, the filter structure of the bushing according to one embodiment can include at least one capacitor, one inductor and/or one electromagnetic resonator as described in the above-mentioned application, "Ceramic bushing with filter", and/or at least one frequency-selective component as described in the above-mentioned application, "Ceramic bushing with filter".

The filter structure in one embodiment forms a band-stop filter or a low-pass filter of first, second or third order. The filter structure includes, for example, an LC anti-resonant circuit, for example an LC anti-resonant circuit according to the description provided above. The LC anti-resonant circuit is arranged in series with the electrically conductive connection, in one embodiment in series within the electrically conductive connection. The filter structure can further include an LC resonant circuit that is connected to the electrically conductive connection between the internal space and the external space as a dissipation filter. The LC resonant circuit includes at least one inductor that is formed by the conducting element.

Moreover, the filter structure can include a continuity filter in a T-arrangement with two serial inductors and one parallel capacitor arranged in between. At least one of the two serial inductors is provided by the conducting element. Moreover, the filter structure can include a continuity filter in a—arrangement with two parallel capacitors and one serial inductor arranged in between. In this context, the serial inductor is provided by the conducting element.

Moreover, the filter structure can include an additional electromechanical dissipation filter or an additional electromechanical serial filter. Filter structures including at least one capacitor include at least one capacitor with at least one electrode surface that is provided by the conducting element. A capacitor of this type can further include a dielectric layer that is provided by the base body. Moreover, a filter structure that includes a capacitor or an electromechanical dissipation filter can provide same as additional frequency-selective component that includes an independent body or an independent housing. Moreover, the filter structure can include multiple inductors of which at least one is provided by the conducting element, whereas at least one further inductor is provided by an independent coil, for example in the form of a wire coil, with or without magnetic core, or in the form of an inductor that is provided as an independent body, for example as an SMD component.

According to another embodiment, the electrical bushing includes multiple conducting elements. The multiple conducting elements each form at least one conducting section of the at least one inductor of the filter structure. In this context, an inductor with multiple tappings can be considered as a single inductor.

The conducting section of the inductor can be surrounded, in part or fully, by a magnetic material in order to attain a higher inductance value. The magnetic material can be magnetically soft and in one embodiment have a complex permeability with a real part of at least 200 or 500 and an imaginary part of at least $1/1000$ or at least $1/100$ of the real part of the complex permeability. Through the high real part $\gg 1$, a multiplication of the inductance value as compared to the inductor in free space is achieved. The imaginary part being larger than 0 results in magnetization losses that are used to attenuate undesired signal components. The magnetic material can surround the conducting section of the inductor in the shape of a ring. In this context, the conducting section can extend along a straight line, whereby it is preferred in one embodiment though for the at least one conducting section to have a longitudinal extension that deviates from a straight line. The magnetic material can be introduced into the base body green compact in the form of a green compact, in pre-sintered or sintered form, and/or can be arranged around the conducting element and/or the conducting element green compact in the scope of a manufacturing method.

Moreover, one embodiment is implemented through a housing for an implantable medical device that includes at least one of the electrical bushings according to one embodiment.

Moreover, one embodiment is implemented through an implantable medical device, for example, a cardiac pacemaker or defibrillator, having at least one electrical bushing according to in one embodiment.

Moreover, one embodiment is implemented through at least one cermet-containing conducting element in an electrical bushing for an implantable medical device for provision of at least one conducting section of an inductor of an electrical filter structure of the bushing.

And lastly, one embodiment is implemented through a method for the manufacture of an electrical bushing for an implantable medical device. The method includes the following steps:

a. generating at least one base body green compact for at least one base body from an electrically insulating material;

b. forming at least one cermet-containing conducting element green compact for at least one conducting element;

c. introducing the at least one conducting element green compact into the base body green compact;

d. subjecting the base body green compact with the at least one base body green compact to firing in order to obtain at least one base body with at least one conducting element.

The method further provides a step of providing an electrical filter structure of the electrical bushing. Step b. includes the forming of at least one section of the conducting element green compact as a conducting section of an inductor of the filter structure.

The conducting element green compact can be formed while the same is being introduced into the base body green compact or before same is being introduced into the base body green compact. In one embodiment, the base body green compact is provided prior to introducing the conducting element green compact, but it can also be produced concurrently with the forming and/or introducing of the conducting element green compact. The base body green compact is subjected to firing jointly with the at least one conducting element green compact, in one embodiment after the conducting element green compact has been introduced into the base body green compact.

One embodiment of the method entails that the step of providing the filter structure includes the step of providing a capacitor element. In this context, a capacitor element is provided in the form of a capacitor whose at least one electrode surface is provided by a section of the conducting element. The capacitor therefore includes at least one electrode surface that is provided by a section of the conducting element. A dielectric layer of the capacitor is formed by a section of the base body. Both the electrode surface and the dielectric layer are provided by planar forming of sections of the conducting element green compact and of the base body green compact. The at least one electrode surface is provided, for example, through planar forming of at least one section of the conducting element green compact. The dielectric layer is provided likewise through planar forming of sections of the base body green compact. Moreover, a section of the conducting element green compact is formed as connection section. The connection section is formed such that it is set up to physically connect the capacitor element to the conducting section of the inductor. Accordingly, a section of the conducting element green compact is formed as connection section, whereby said connection section provides the physical connection of capacitor element and conducting element after the firing or sintering. Since the connection section is provided as a section of the conducting element green compact and is cermet-containing, the connection section is electrically conductive after sintering and connects the capacitor element to the inductor and/or the conducting section of the inductor after sintering in an electrically conductive manner. The connection section and the capacitor and the inductor are formed such that an LC anti-resonant circuit is formed. Alternatively, the connection section is formed in such a manner and connected to the capacitor and the inductor that an LC resonant circuit results due to the interconnection of the capacitor and inductor through the connection section.

Accordingly, the manufacturing method can provide that a section of the conducting element green compact is formed as an electrode surface in order to provide a capacitor after the step of firing, which capacitor is provided at least in part by a section of the conducting element. Since, according to in one embodiment, a section of the conducting element green compact also is formed as conducting section of an inductor, the forming of sections of the conducting element can generate different types of components through structuring the conducting element and/or base body. In order to connect said components, a connecting element is generated, in one embodiment also through forming a section of the conducting element. By this means, the forming of sections of the conducting element and at least one section of the base body generates a filter structure with multiple components. The forming of sections of the base body and conducting element allows, for example, a filter structure forming a higher order filter to be generated.

In addition, one embodiment can provide that additional physically independent components are inserted into the electrical bushing and become part of the filter structure. This is enabled in that a section of the conducting element is provided as contact surface, in one embodiment by planar forming of a section of the conducting element. A physically independent component can then be attached to the filter structure through said contact surface and thus become part of the filter structure. The physically independent component corresponds, for example, to the individual component described herein.

In this context, one embodiment further provides that the step of providing the filter structure includes the providing of the conducting element as at least one contact surface. The method further provides for introducing at least one pre-made frequency-selective component into the conducting element green compact or into the base body green compact. Alternatively, at least one pre-made frequency-selective component is arranged on a section of the conducting element green compact or on a section of the base body green compact. Moreover, the at least one frequency-selective component is connected to the at least one contact surface. The frequency-selective component is introduced and connected before or after the conducting element green compact is introduced into the base body green compact. Alternatively, the method also provides for arranging at least one pre-made frequency-selective component on or in the base body and connecting it to the conducting element after the step of firing has been carried out.

In this context, the frequency-selective component is a physically independent component, for example, a pre-made component. The frequency-selective component is already equipped with connectors before connecting it to the contact surface and/or before arranging it on or in the base body green compact or the conducting element green compact. Accordingly, the pre-made component can be connected to the green compact before the step of firing is carried out or it can be connected to the conducting element and/or the base body after the firing or after a pre-sintering process. For example, the pre-made component is electrically connected to the contact surface after the firing and/or after completion of all pre-sintering processes.

The base body and the conducting element are hermetically sealed to each other through establishing a firmly bonded connection between base body and conducting element. This is attained, for example, through sintering after the base body green compact and the conducting element green compact have been made to contact each other. Introducing the at least one conducting element green compact into the base body green compact entails that the conducting element green compact and the base body green compact are made to be in direct contact to each other.

The at least one section of the conducting element green compact is formed as a conducting section of an inductor through rendering same to have a shape as described through the description of shapes of the conducting section above. The conducting element green compact can be pre-sintered before introducing it into the base body green compact. This attains a certain stability such that the shape of the conducting element green compact is not changed inadvertently while introducing it.

Moreover, if desired, a holding element made from a cermet can be provided, whereby a holding element green compact extends around the base body or green compact thereof, and is sintered. A corresponding electrical bushing therefore further includes a holding element that extends around the circumference of the base body.

And lastly, one embodiment provides a method, in which a housing having an electrical bushing is generated by initially producing the housing as a green compact, in one embodiment from a cermet-containing material, whereby the electrical bushing is introduced into the housing and, for example, into a housing wall of the housing before or after a sintering step. In this context, the housing can be pre-sintered or be provided as a green compact when the electrical bushing is introduced as a green compact.

In summary, the following embodiments are proposed:

The proposed electrical bushing is set up for use in an implantable medical device, whereby the implantable medical device can be provided, in one embodiment, as an active implantable medical device (AIMD) and in one embodiment as a therapeutic device.

As a matter of principle, the term, implantable medical device, shall include any device which is set up to perform at least one medical function and which can be introduced into a body tissue of a human or animal user. As a matter of principle, the medical function can include any function selected from the group consisting of a therapeutic function, a diagnostic function, and a surgical function. For example, the medical function can include at least one actuator function, in which an actuator is used to exert at least one stimulus on the body tissue, for example, an electrical stimulus.

As a matter of principle, the term, active implantable medical device—also called AIMD—shall include all implantable medical devices that can conduct electrical signals from a hermetically sealed housing to a part of the body tissue of the user and/or receive electrical signals from the part of the body tissue of the user. Accordingly, the term, active implantable medical device, includes, for example, cardiac pacemakers, cochlea implants, implantable cardioverters/defibrillators, nerve, brain, organ or muscle stimulators as well as implantable monitoring devices, hearing aids, retinal implants, muscle stimulators, implantable drug pumps, artificial hearts, bone growth stimulators, prostate implants, stomach implants or the like.

The implantable medical device, for example, the active implantable medical device, can usually include, for example, at least one housing, for example, at least one hermetically sealed housing. The housing can in one embodiment enclose at least one electronics unit, for example a triggering and/or analytical electronics unit of the implantable medical device.

In the scope of one embodiment, a housing of an implantable medical device shall be understood to be an element that encloses, at least in part, at least one functional element of the implantable medical device that is set up to perform the at least one medical function or promotes the medical function. For example, the housing includes at least one internal space that takes up the functional element fully or in part. For example, the housing can be set up to provide mechanical protection to the functional element with respect to strains occurring during operation and/or upon handling, and/or provide protection to the functional element with respect to ambient influences such as, for example, influences of a body fluid. The housing can, for example, border and/or close the implantable medical device with respect to the outside.

In this context, an internal space shall be understood herein to mean a region of the implantable medical device, for example, within the housing, which can take up the functional element fully or in part and which, in an implanted state, does not contact the body tissue and/or a body fluid. The internal space can include at least one hollow space which can be closed fully or in part. However, alternatively, the internal space can be filled up fully or in part, for example by the at least one functional element and/or by at least one filling material, for example at least one casting, for example at least one casting material in the form of an epoxy resin or a similar material.

An external space, in contrast, shall be understood to be a region outside of the housing. This can, for example, be a region which, in the implanted state, can contact the body tissue and/or a body fluid. Alternatively or in addition, the external space can just as well be or include a region that is only accessible from outside the housing without necessarily contacting the body tissue and/or the body fluid, for example a region of a connecting element of the implantable medical device that is accessible from outside to an electrical connecting element, for example an electrical plug connector.

The housing and/or, for example, the electrical bushing can, for example, be provided to be hermetically sealed such that, for example, the internal space, is hermetically sealed with respect to the external space. In this context, the term, "hermetically sealed", can illustrate that moisture and/or gases cannot permeate through the hermetically sealed element at all or only to a minimal extent upon intended use for the common periods of time (for example 5-10 years). The leakage rate, which can be determined, for example, by leak tests, is a physical parameter that can described, for example, a permeation of gases and/or moisture through a device, for example, through the electrical bushing and/or the housing. Pertinent leak tests can be carried out with helium leak testers and/or mass spectrometers and are specified in the Mil-STD-883G Method 1014 standard. In this context, the maximal permissible helium leak rate is determined as a function of the internal volume of the device to be tested. According to the methods specified in MIL-STD-883G, method 1014, section 3.1 and taking into consideration the volumes and cavities of the devices to be tested that are used in the application of one embodiment, said maximal permissible helium leak rates can, for example, be from $1 \times 10^{-8}$ atm*cm$^3$/sec to $1 \times 10^{-7}$ atm*cm$^3$/sec. In the scope of one embodiment, the term, "hermetically sealed", shall be understood, for example, to mean that the device to be tested (for example the housing and/or the electrical bushing and/or the housing with the electrical bushing) has a helium leak rate of less than $1 \times 10^{-7}$ atm*cm$^3$/sec. In one embodiment, the helium leak rate can be less than $1 \times 10^{-8}$ atm*cm$^3$/sec, in one embodiment, less than $1 \times 10^{-9}$ atm*cm$^3$/sec. For the purpose of standardization, the above-mentioned helium leak rates can also be converted into the equivalent standard air leak rate. The definition of the equivalent standard air leak rate and the conversion are specified in the ISO 3530 standard.

Electrical bushings are elements set up to create at least one electrically conducting path that extends between the internal space of the housing to at least one external point or region outside the housing, for example, situated in the external space. Accordingly, this establishes, for example, an electrical connection to leads, electrodes, and sensors that are arranged outside the housing.

Common implantable medical devices are commonly provided with a housing, which can include, on one side, a head part, also called header or connecting body, that carries connection sockets for connection of leads, also called electrode leads. The connection sockets include, for example, electrical contacts that serve to electrically connect the leads to a control electronics unit on the interior of the housing of the medical device. Usually, an electrical bushing is provided in the location, at which the electrical connection enters into the housing of the medical device, and the electrical bushing is inserted into a corresponding opening of the housing in a hermetically sealing manner.

Due to the type of use of implantable medical devices, their hermetic sealing and biocompatibility are usually amongst the foremost requirements. The implantable medical device proposed herein according to one embodiment, can be inserted, for example, into a body of a human or animal user, for example, of a patient. As a result, the implantable medical device is usually exposed to a fluid of a body tissue of the body. Accordingly, it is usually important that no body fluid penetrates into the implantable medical device and that no liquids leak from the implantable medical device. In order to ensure this, the housing of the implantable medical device, and thus the electrical bushing as well, should be as impermeable as possible, for example, with respect to body fluids.

Moreover, the electrical bushing should ensure high electrical insulation between the at least one conducting element and the housing and/or the multiple conducting elements provided that more than one conducting element are present. In this context, the insulation resistance reached in one embodiment is at least several MOhm, in one embodiment, more than 20 MOhm, and the leakage currents reached can be small, in one embodiment, less than 10 pA. Moreover, in case multiple conducting elements are present, the crosstalk and electromagnetic coupling between the individual conducting elements in one embodiment are below the specified thresholds for medical applications.

The electrical bushing disclosed according to one embodiment is well-suited for the above-mentioned applications. Moreover, the electrical bushing can also be used in other applications that are associated with special requirements with regard to biocompatibility, tight sealing, and stability.

The electrical bushing according to one embodiment can meet, for example, the above-mentioned tight sealing requirements and/or the above-mentioned insulation requirements.

As mentioned above, the electrical bushing includes at least one electrically insulating base body. In the scope of one embodiment, a base body shall be understood to mean an element that serves a mechanical holding function in the electrical bushing, for example in that the base body holds or carries the at least one conducting element either directly or indirectly. For example, the at least one conducting element can be embedded in the base body directly or indirectly, fully or partly, for example, through a firmly bonded connection between the base body and the conducting element and in one embodiment through co-sintering of the base body and the conducting element. For example, the base body can have at least one side facing the internal space and at least one side facing the external space and/or accessible from the external space.

As mentioned above, the base body is provided to be electrically insulating. This means that the base body, fully or at least regions thereof, is made from at least one electrically insulating material. In this context, an electrically insulating material shall be understood to mean a material with a resistivity of at least $10^7$ Ohm*m, in one embodiment, of at least $10^8$ Ohm*m, in one embodiment of at least $10^9$ Ohm*m, and in one embodiment of at least $10^{11}$ Ohm*m. For example, the base body can be provided such that, as mentioned above, a flow of current between the conducting element and the housing and/or between multiple conducting elements is at least largely prevented, for example through the resistivity values between the conducting element and the housing as specified above being implemented. For example, the base body can include at least one ceramic material.

In this context, a conducting element or electrical conducting element shall generally be understood to mean an element set up to establish an electrical connection between at least two sites and/or at least two elements. For example, the conducting element can include one or more electrical conductors, for example metallic conductors. In the scope of the one embodiment, the conducting element is made fully or partly of at least one cermet, as mentioned above. In addition, one or more other electrical conductors, for example metallic conductors, can be provided. The conducting element can, for example, be provided in the form of one or more contact pins and/or curved conductors. Moreover, the conducting element can include, for example, on a side of the base body and/or electrical bushing facing the internal space or on a side of the base body and/or electrical bushing facing the external space or accessible from the external space, one or more connecting contacts, for example one or more plug-in connectors, for example one or more connecting contacts, which project from the base body or can be electrically contacted through other means from the internal space and/or the external space.

The at least one conducting element can establish the electrically conducting connection between the internal space and the external space in a variety of ways. For example, the conducting element can extend from at least one section of the conducting element that is arranged on the side of the base body facing the internal space to at least one section of the conducting element arranged on the side facing the external space or accessible from the external space. However, other arrangements are also feasible as a matter of principle. Accordingly, the conducting element can just as well include a plurality of partial conducting elements that are connected to each other in an electrically conducting manner. Moreover, the conducting element can extend into the internal space and/or the external space. For example, the conducting element can include at least one region that is arranged in the internal space and/or at least one region that is arranged in the external space, whereby the regions can, for example, be electrically connected to each other. Various exemplary embodiments shall be illustrated in more detail below.

The at least one conducting element can include, on a side of the base body and/or electrical bushing facing the internal space or on a side of the base body and/or electrical bushing facing the external space or accessible from the external space, at least one electrical connecting element and/or be connected to an electrical connecting element of this type. For example, as described above, one or more plug-in connectors and/or one or more contact surfaces and/or one or more contact springs and/or one or more types of electrical connecting elements can be provided on one or both of said sides. The at least one optional connecting element can, for example, be a component of the at least one conducting element and/or can be connected to the at least one conducting element in an electrically conducting manner. For example, one or more conducting elements of the bushing can be contacted to one or more internal connecting elements and/or one or more external connecting elements. The material of the internal connecting elements should be suited for permanent connection to the conducting element. The external connecting elements should be biocompatible and should be such that they can be permanently connected to the at least one conducting element.

The electrically insulating base body can support, as a bearing, for example, the at least one conducting element. The at least one material of the base body should in one embodiment be biocompatible, as illustrated above, and should have sufficiently high insulation resistance. It has proven to be advantageous in one embodiment for the base body to include one or more materials selected from the group consisting of: aluminum oxide ($Al_2O_3$), zirconium dioxide ($ZrO_2$), aluminum oxide-toughened zirconium oxide (ZTA), zirconium oxide-toughened aluminum oxide (ZTA—Zirconia Toughened Aluminum—$Al_2O_3/ZrO_2$), yttrium-toughened zirconium oxide (Y-TZP), aluminum nitride (AlN), magnesium oxide (MgO), piezoceramic materials, barium (Zr, Ti) oxide, barium (CE, Ti) oxide, and sodium-potassium-niobate.

A holding element reaches around the base body and serves as connecting element to the housing of the implantable device. The materials of the edge body must be biocompatible, easy to process, corrosion-resistant, and permanently connectable to the base body and the housing in a firmly bonded manner. It has proven to be advantageous in one embodiment for the edge body according to one embodiment to include at least one of the following metals and/or an alloy based on at least one of the following metals: platinum, iridium, niobium, molybdenum, tantalum, tungsten, titanium, cobalt-chromium alloys or zirconium.

In the proposed electrical bushing, the at least one conducting element includes at least one cermet.

The base body can, for example, be made fully or partly from one or more sinterable materials, for example, from one or more ceramic-based sinterable materials. The conducting element or elements can fully or partly be made of one or more cermet-based sinterable materials. Moreover, the at least one conducting element can also, as mentioned above, include one or more additional conductors, for example one or more metallic conductors.

In the scope of one embodiment, "cermet" shall refer to a composite material made of one or more ceramic materials in at least one metallic matrix or a composite material made of one or more metallic materials in at least one ceramic matrix. For production of a cermet, for example, a mixture of at least one ceramic powder and at least one metallic powder can be used to which, for example, at least one binding agent and, if applicable, at least one solvent can be added. The ceramic powder or powders of the cermet in one embodiment has or have a mean grain size of less than 10 µm, in one embodiment less than 5 µm, and in one embodiment less than 3 µm. The metallic powder or powders of the cermet in one embodiment have a mean grain size of less than 15 µm, in one embodiment less than 10 µm, and in one embodiment less than 5 µm. For production of a base body, for example, at least one ceramic powder can be used to which, for example, at least one binding agent and, if applicable, at least one solvent can be added. In this context, the ceramic powder or powders in one embodiment has/have a mean grain size of less than 10 µm (1 µm are equal to $1\times10^{-6}$ m), in one embodiment less than 5 µm, in one embodiment less than 3 µm. For example, the median value or the d50 value of the grain size distribution is considered to be the mean grain size in this context. The d50 value corresponds to the value at which 50 percent of the grains of the ceramic powder and/or metallic powder are finer and 50% are coarser than the d50 value.

In the scope of one embodiment, sintering or a sintering process shall generally be understood to mean a method for producing materials or work-pieces, in which powdered, in particular fine-grained, ceramic and/or metallic substances are heated and thus connected. This process can proceed without applying external pressure onto the substance to be heated or can, for example, proceed under elevated pressure onto the substance to be heated, for example under a pressure of at least 2 bar, in one embodiment higher pressures, for example pressures of at least 10 bar, for example, at least 100 bar, or even at least 1000 bar. The process can proceed, for example, fully, or partly at temperatures below the melting temperature of the powdered material, for example at temperatures of 700° C. to 1400° C. The process can be implemented, for example, fully, or partly in a tool and/or a mould such that a forming step can be associated with the sintering process. Aside from the powdered materials, a starting material for the sintering process can include further materials, for example one or more binding agents and/or one or more solvents. The sintering process can proceed in one or more steps, whereby additional steps can precede the sintering process, for example one or more forming steps and/or one or more debinding steps.

A method can be used, for example, in the manufacture of the at least one conducting element and/or optionally in the manufacture of the at least one base body, in which at least one green compact is manufactured first, subsequently at least one brown compact is manufactured from said green compact, and subsequently the finished work-piece is manufactured from said brown compact through at least one sintering step. In this context, separate green compacts and/or separate brown compacts can be manufactured for the conducting element and the base body and can be connected subsequently. Alternatively, one or more common green compacts and/or brown compacts can be produced for the base body and the conducting element. Alternatively again, separate green compacts can be produced first, said green compacts can then be connected, and subsequently a common brown compact can be produced from the connected green compact. In general, a green compact shall be understood to mean a pre-form body of a work-piece which includes the starting material, for example the at least one ceramic and/or metallic powder, as well as, if applicable, the one or more binding agents and/or one or more solvents. A brown compact shall be understood to mean a pre-form body which is generated from the green compact through at least one debinding step, for example at least one thermal and/or chemical debinding step, whereby the at least one binding agent and/or the at least one solvent is/are removed, at least partly, from the pre-form body in the debinding step.

The sintering process, for example, of a cermet, but of the base body just as well, for example, can proceed comparable to a sintering process that is commonly used for homogeneous powders. For example, the material can be compacted in the sintering process at high temperature and, if applicable, high pressure such that the cermet is virtually sealed tight or has no more than closed porosity. Usually, cermets are characterized by their particularly high toughness and wear resistance. Compared to sintered hard metals, a cermet-containing transmission element usually has a higher thermal shock and oxidation resistance and usually a thermal expansion coefficient that is matched to a surrounding insulator.

For the bushing according to one embodiment, the at least one ceramic component of the cermet can include, for example, at least one of the following materials: aluminum oxide ($Al_2O_3$), zirconium dioxide ($ZrO_2$), aluminum oxide-toughened zirconium oxide (ZTA), zirconium oxide-toughened aluminum oxide (ZTA—Zirconia Toughened Aluminum—$Al_2O_3/ZrO_2$), yttrium-toughened zirconium oxide (Y-TZP), aluminum nitride (AlN), magnesium oxide (MgO), piezoceramic materials, barium (Zr, Ti) oxide, barium (CE, Ti) oxide, and sodium-potassium-niobate.

For the bushing according to one embodiment, the at least one metallic component of the cermet can include, for example, at least one of the following metals and/or an alloy based on at least one of the following metals: platinum, iridium, niobium, molybdenum, tantalum, tungsten, titanium, cobalt or zirconium. An electrically conductive connection is usually established in the cermet when the metal content exceeds the so-called percolation threshold at which the metal particles in the sintered cermet are connected to each other, at least in spots, such that electrical conduction is enabled. For this purpose, experience tells that the metal content should be 25% by volume and more, in one embodiment 32% by volume, in one embodiment, more than 38% by volume, depending on the selection of materials.

In the scope of one embodiment, the terms, "including a cermet," "cermet-including," "comprising a cermet," and "cermet-containing", are used synonymously. Accordingly, the terms refer to the property of an element, being that the element contains cermet. This meaning also includes the variant of an embodiment in that elements, for example the conducting element, consist of a cermet, that is, are fully made of a cermet.

In one embodiment, both the at least one conducting element and the base body can include one or more components which are or can be manufactured in a sintering procedure, or the at least one conducting element and the base body are or can both be manufactured in a sintering procedure. For example, the base body and the conducting element are or can be manufactured in a co-sintering procedure, that is, a procedure of simultaneous sintering of these elements. For example, the conducting element and the base body each can include one or more ceramic components that are manufactured, and in one embodiment compacted, in the scope of at least one sintering procedure.

For example, a base body green compact can be manufactured from an insulating composition of materials. This can proceed, for example, by compressing the composition of materials in a mould. In this context, the insulating composition of materials in one embodiment is a powder mass, in which the powder particles show at least minimal cohesion. In this context, the production of a green compact proceeds, for example, through compressing powder masses or through forming by plastic shaping or casting and subsequent drying.

Said procedural steps can also be utilized to form at least one cermet-containing conducting element green compact.

In this context, one embodiment can provide that the powder, which is compressed to form the conducting element green compact, is cermet-containing or consists of a cermet or includes at least one starting material for a cermet. Subsequently, the two green compacts—the base body green compact and the conducting element green compact—can be combined. The production of the conducting element green compact and the base body green compact can just as well proceed simultaneously, for example, by multi-component injection molding, co-extrusion, etc., such that there is no longer a need to connect them subsequently.

While the green compacts are being sintered, they are in one embodiment subjected to a heat treatment below the melting temperature of the powder particles of the green compact. This usually leads to compaction of the material and ensuing substantial reduction of the porosity and volume of the green compacts. Accordingly, in one method the base body and the conducting element can in one embodiment be sintered jointly. Accordingly, there is in one embodiment no longer a need to connect the two elements subsequently.

Through the sintering, the conducting element becomes connected to the base body in one embodiment in a positive fit-type and/or non-positive fit-type and/or firmly bonded manner. This in one embodiment achieves hermetic integration of the conducting element into the base body. In one embodiment, there is no longer a need for subsequent soldering or welding of the conducting element into the base body. Rather, a hermetically sealing connection between the base body and the conducting element is attained through the joint sintering in one embodiment and utilization of a cermet-containing green compact in one embodiment.

One refinement of the method is characterized in that the sintering includes only partial sintering of the at least one optional base body green compact, whereby said partial sintering can effect and/or include, for example, the debinding step mentioned above. In one embodiment, the green compact is heat-treated in the scope of said partial sintering. This is usually already associated with some shrinkage of the volume of the green compact. However, the volume of the green compact has not yet reached its final state. Rather, another heat treatment is usually needed—a final sintering—in which the green compact(s) is/are shrunk to its/their final size. In the scope of said variant of an embodiment, the green compact is in one embodiment sintered only partly in order to attain a certain stability to render the green compact easier to handle.

The starting material used for producing at least one conducting element green compact and/or at least one base body green compact can, for example, be a dry powder or include a dry powder, whereby the dry powder is compressed in the dry state into a green compact and shows sufficient adhesion to maintain its compressed green compact shape. However, optionally, the starting material can include one or more further components in addition to the at least one powder, for example, as mentioned above, one or more binding agents and/or one or more solvents. Said binding agents and/or solvents, for example organic and/or inorganic binding agents and/or solvents, are generally known to the person skilled in the art, and are commercially available, for example. The starting material can, for example, include one or more slurries or be a slurry. In the scope of one embodiment, a slurry is a suspension of particles of a powder made of one or more materials in a liquid binding agent, and, if applicable, in a water-based or organic binding agent. A slurry has a high viscosity and can easily be formed into a green compact without the application of high pressure, for example through casting or injection molding or plastic forming In the case of green compacts made from slurries, the sintering process, which is generally carried out below the melting temperature of the ceramic, cermet or metal materials that are used, but in individual cases can also be carried out just above the melting temperature of the lower melting component of a multi-component mixture, this usually being the metal component, leads to the binding agent slowly diffusing from the slurry. Overly rapid heating leads to a rapid increase of the volume of the binding agent by transition to the gas phase and destruction of the green compact or formation of undesired defects in the workpiece.

Thermoplastic and duroplastic polymers, waxes, thermogelling substances and/or surface-active substances, for example, can be used as binding agent—also called binder. In this context, these can be used alone or as binding agent mixtures of multiple components of this type. If individual elements or all elements of the bushing (base body green compact, conducting element green compact, bushing blank) are produced in the scope of an extrusion procedure, the composition of the binding agent should be such that the line of the elements extruded through the nozzle is sufficiently stable in shape for the shape defined by the nozzle to easily be maintained. Suitable binders, also called binding agents, are known to the person skilled in the art.

In contrast to one embodiment, according to which a conducting element includes at least one cermet, the prior art has a metallic wire or other metallic work-piece be the conducting element. A conducting element, which, according to one embodiment, is provided with a cermet, can be connected to the base body easily, since the cermet and the insulation element are or include ceramic substances and/or a ceramic material. The base body can also be called insulation element in order to address the electrical function; in this context, the two terms are exchangeable. Green compacts of both the conducting element and the base body can be produced and subsequently subjected to a sintering process. The resulting electrical bushing is not only particularly biocompatible and durable, but also possesses good hermetic sealing properties. Thus, no fissures or connecting sites still to be soldered result between the conducting element and the base body. Rather, sintering results in the base body and the conducting element becoming connected. One variant of an embodiment, therefore provides the at least one conducting element to consist of a cermet. In this variant of an embodiment, the conducting element includes not only components made of cermet, but is fully made of a cermet.

Generally, cermets are characterized by their particularly high toughness and wear resistance. The "cermets" and/or "cermet-containing" substances can, for example, be or include cutting materials related to hard metals which can dispense with tungsten carbide as the hard substance and can be produced, for example, by a powder metallurgical route. A sintering process for cermets and/or the cermet-containing conducting element proceeds, for example, alike a process for homogeneous powders except that, at identical compression force, the metal is usually compacted more strongly than the ceramic material. Compared to sintered hard metals, the cermet-containing conducting element usually shows higher resistance to thermal shock and oxidation. As mentioned above, the ceramic components can be, for example, aluminum oxide ($Al_2O_3$) and/or zirconium dioxide ($ZrO_2$), whereas for example, niobium, molybdenum, titanium, cobalt, zirconium, chromium are conceivable as metallic components.

For integration of the electrical bushing into the housing of a cardiac pacemaker, the electrical bushing can include a holding element. Said holding element is wreath-shaped and/or arranged around the base body in the form of a continuous rim, in one embodiment circumferential. The holding element surrounds the base body, in one embodiment along its entire circumference. The purpose of the holding element is to establish a non-positive fit- and/or positive fit-type connection to the housing. A fluid-tight connection between the holding element and the housing must be established in the process. In one embodiment, the electrical bushing includes a holding element that includes a cermet. The cermet-containing holding element can be connected to the housing of the implantable medical device in an easy, durable and hermetically sealed manner. Another embodiment provides the holding element to not only include a cermet, but to consist of a cermet. Moreover, it is conceivable that the conducting element and the holding element are made from the same material. In this variant, the same materials are used for both the conducting element and the holding element. This relates, for example, to a durable, conductive, and biocompatible cermet. Since both the holding element and the conducting element are still to be connected to metallic components, both must include means to be welded or soldered to them. If a cermet is found that meets the pre-requisites specified above, said cermet can be used for both the holding element and the conducting element in order to obtain a particularly inexpensive electrical bushing.

In electrical terms, the base body can also be considered to be an insulation element that is electrically insulating. The base body is made from an electrically insulating material, in one embodiment from an electrically insulating composition of materials. The base body is set up to electrically insulate the conducting element from the holding element or—(in case no holding element is provided)—from the housing and/or other objects of the implantable medical device. Electrical signals that are propagated through the conducting wire shall not be attenuated or short-circuited by contacting the housing of the implantable device. In addition, the composition of the base body must be biocompatible for implantation in medical applications. For this reason, it is preferred in one embodiment that the base body consists of a glass-ceramic or glass-like material. It has been found to be preferred in one embodiment that the insulating composition of materials of the base body is at least any one from the group, aluminum oxide ($Al_2O_3$), magnesium oxide (MgO), zirconium oxide ($ZrO_2$), aluminum titanate ($Al_2TiO_5$), and piezoceramic materials. In this context, aluminum oxide features high electrical resistance and low dielectric losses. These properties are supplemented by the additional high thermal resistance and good biocompatibility.

Another refinement of the bushing according to one embodiment is characterized in that the holding element includes at least one flange, whereby the flange, for example, is conductive like a metal. The purpose of the flange is to seal the electrical bushing with respect to a housing of the implantable device. The holding element holds the electrical bushing in the implantable device. In the variant of an embodiment described herein, the holding element includes at least one flange on an external side. These flanges form a bearing, which can be engaged by the lids of the implantable medical device, in particularly engaged in a tightly sealing manner. Accordingly, the holding element including the flanges connected to it can have a U- or H-shaped cross-section. Integrating at least one flange into the holding element ensures that the electrical bushing is integrated into the implantable device in a safe, impact-resistant and durable manner. In addition, the flanges can be provided such that the lids of the implantable device are connected clip-like to the holding element in a non-positive fit-type or positive fit-type manner.

Another refinement of the electrical bushing according to in one embodiment is characterized in that the at least one flange includes a cermet. In the scope of said variant of an embodiment, both the holding element and the flange include a cermet. Both the flange and the holding element are made of the same material in one embodiment. By providing the flange as a cermet, the flange can be sintered easily and inexpensively as part of the holding element jointly with the insulation element and the conducting element in the scope of the method to be described below.

One embodiment also includes a use of at least one cermet-including conducting element in an electrical bushing for an implantable medical device. Features and details that were described in the context of the electrical bushing and/or the method shall obviously also apply in relation to the use of a cermet-containing conducting element.

The scope of one embodiment also includes an implantable medical device, for example, a cardiac pacemaker or defibrillator, having an electrical bushing according to at least one of the preceding claims. Features and details that were described in the context of the electrical bushing and/or the method shall obviously also apply in relation to the implantable medical device.

Features and properties that are described in the context of the electrical bushing shall also apply in relation to the method according to one embodiment, and vice versa.

The method according to one embodiment provides both the base body and the conducting element to include ceramic components that are processed in the scope of a sintering process. In the scope of step a), a base body green compact is generated from an insulating composition of materials. This can be done by compressing the composition of materials in a mould. In this context, the insulating composition of materials in one embodiment is a powder mass, in which the powder particles show at least minimal cohesion. Usually, this is effected in that a grain size of the powder particles does not exceed 0.5 mm. In one embodiment, the mean grain size is no larger than 10 µm. In this context, the manufacture of the green compact proceeds either by compressing powder masses or by forming and subsequent drying. Said procedural steps are also utilized to form the cermet-containing conducting element green compact. In this context, one embodiment provides the powder, which is compressed into the conducting element green compact, to be cermet-containing or to consist of a cermet. The green compacts—for example, the base body green compact and the conducting element green compact—are in one embodiment combined subsequent to this step. After this step, which is called step c), the two green compacts are subjected to firing—which is also called sintering. In the process of sintering or firing, the green compacts are subjected to a heat treatment below the melting temperature of the powder particles of the green compact. This leads to a substantial reduction of the porosity and volume of the green compacts. The special feature according to one embodiment of the method is therefore that the base body and the conducting element are jointly subjected to firing and the conducting element is generated to have at least one conductive surface.

Subsequently, there is no longer a need to connect the two elements and, for example, there is no need to generate a conductive surface in an additional step. Through the firing process, the conducting element becomes connected to the base body in a positive fit-type and/or non-positive fit-type and/or firmly bonded manner. This achieves hermetic integration of the conducting element into the base body. There is no longer a need for subsequent soldering or welding of the conducting element into the base body. Rather, through the joint firing and the utilization of a cermet-containing green compact, that is, of the conducting element green compact, a hermetically sealing connection between the base body and the conducting element is attained.

One refinement of the method according to one embodiment is characterized in that step a) includes a partial sintering of the base body green compact. The green compact of the insulation element is heat-treated in the scope of said partial sintering. This is already associated with some shrinkage of the volume of the insulation element green compact. However, the volume of the green compact does not reach its final state. Rather, this requires another heat treatment in the scope of step d), in which the base body green compact and the conducting element green compact are shrunk to their final size. In the scope of said variant of an embodiment, the green compact is heat treated only partly in order to already attain a certain surface hardness to render the base body green compact easier to handle. This is expedient in particular in the case of insulating compositions of materials which can be compressed into a green compact shape only with some difficulty.

For example, a component of the bushing according to one embodiment is called green compact unless all sintering steps have been carried out. Accordingly, even a pre-sintered or partly sintered or heat-treated green compact is called green compact until all heat treatment or sintering steps have been completed.

Another variant of the embodiment is characterized in that the conducting element green compact is also already partly sintered in step b). As described above for the base body green compact, the conducting element green compact can also be partly sintered in order to already attain a certain surface stability. It needs to be noted in this context that the final complete sintering occurs no earlier than in step d). Accordingly, the conducting element green compact attains its final size only in step d).

Another refinement of the method is characterized in that at least one cermet-containing holding element green compact for a holding element is generated. The conducting element green compact is introduced into the base body green compact. The base body green compact is introduced into the holding element green compact. The base body green compact is subjected to firing jointly with the at least one conducting element green compact and the holding element green compact. This results in a base body with a conducting element and a holding element.

The special feature of this procedural step is that, not only the conducting element green compact and the base body green compact, but also the holding element green compact is sintered in one step. All three green compacts are generated, then joined, and subsequently subjected to firing or sintering as a unit. In a particular variant of an embodiment, producing the at least one cermet-containing holding element green compact can include a partial sintering. As before, one embodiment provides the fringe green compact to be partly sintered in order to attain higher surface stability. In this context, the base body green compact can thus form the dielectric layer or a piezoelectric body for the filter structure or a receptacle for a frequency-selective component.

A specific exemplary embodiment of a method for the manufacture of a bushing according to one embodiment is presented in the following.

In the first step, a cermet mass is produced from platinum (Pt) and aluminum oxide ($Al_2O_3$) containing 10% zirconium dioxide ($ZrO_2$). The following starting materials are used for this purpose:

40 vol. % Pt powder with a mean grain size of 10 μm, and
60 vol. % $Al_2O_3/ZrO_2$ powder with a relative $ZrO_2$ content of 10% and a mean grain size of 1 μm.

The two components were mixed, water and a binding agent were added, and the sample was homogenized through a kneading process. Analogous to the first step, a ceramic mass is produced in a second step from a powder with an $Al_2O_3$ content of 90% and a $ZrO_2$ content of 10%. The mean grain size was approx. 1 μm. As before, water and a binding agent were added to the ceramic powder and the sample was homogenised. In a third step, the ceramic mass made of aluminium oxide with a 10% zirconium dioxide content produced in step two was converted to a shape of a base body. Made from the cermet mass produced in the first step, a cermet body that contained a mixture of platinum powder and aluminium oxide with a zirconium dioxide content of 10%, was introduced as green compact into an opening in the base body green compact. Subsequently, the ceramic mass was compacted in the mould. Then the cermet and the ceramic component were subjected to debinding at 500° C. and the sintering was finished at 1650° C.

Figure 1:
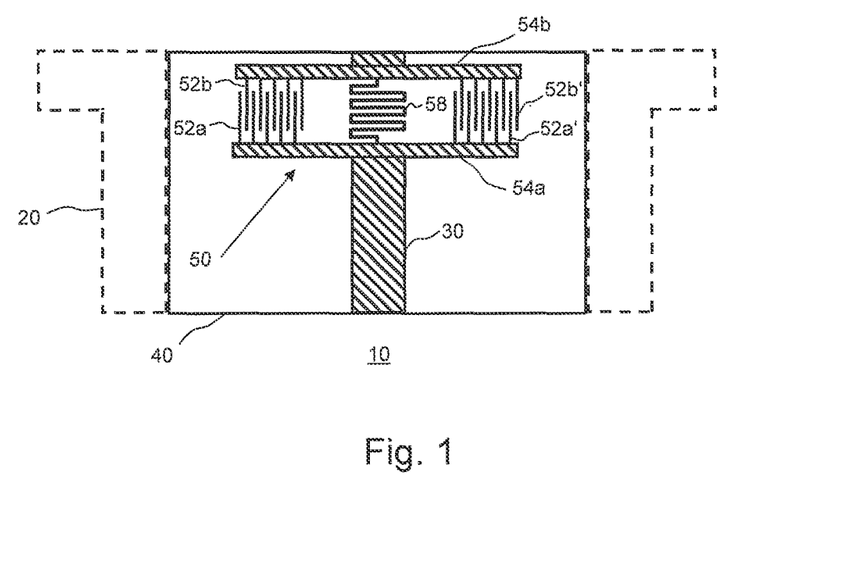
FIG. 1 illustrates a first embodiment of the electrical bushing according to one embodiment.

FIG. 1 illustrates a first embodiment of the electrical bushing 10. It can be surrounded by a holding element 20, whereby the optional holding element 20 is indicated through dashed lines. The electrical bushing 10 includes a conducting element 30 and a base body 40. The conducting element 30 is provided in said base body 40. The electrical bushing 10 illustrated in FIG. 1 further includes a filter structure 50 that is provided by sections of the conducting element. A first capacitor is formed by a first group of electrodes 52a and a second group of electrodes 52b which each are shifted radially with respect to the longitudinal axis of the electrical bushing. The electrode surfaces of the group of electrodes 52a each are situated opposite from the electrode surfaces of the group of electrodes 52b, and the dielectric layers extend between the respective electrode surfaces. The dielectric layers are provided by sections of the base body 40. The groups of electrodes 52a and 52b thus form two poles of the capacitor. The capacitor therefore has a multi-layered structure. The electrode surfaces 52a and 52b extend along the longitudinal axis of the electrical bushing, that is, along the extension of the electrically conductive connection which is provided by the conducting element 30. The electrode surfaces of the groups of electrodes 52a and b are provided by sections of the conducting element 30 and thus include a cermet. A further capacitor is provided by third and fourth groups of electrodes 52a' and 52b' which are arranged symmetrical thereto. The group of electrodes 52a includes electrode surfaces that are opposite to electrode surfaces of group of electrodes 52'. Multiple dielectric layers are situated between the groups of electrodes 52a' and 52b'. The dielectric layers are provided by sections of the base body 40. A first connection section 54a connects the groups of electrodes 52a and 52a' and a second connection section 54b connects the groups of electrodes 52b and 52b'. The connection sections 54a and 54b each extend perpendicular to the longitudinal axis of the electrical bushing and are plane parallel to each other. The connection sections 54a and 54b do not only connect the electrode surfaces, but also provide an electrical connection to the longitudinal sections of the conducting element 30. This results in a first long longitudinal section below the connection section 54a and a short longitudinal section above the connection section 54b.

In order to provide the electrically conductive connection, an inductor 58 is situated between the connection sections 54a and 54b and/or between the longitudinal sections of the conducting element 30 described above. The inductor 58 includes multiple longitudinal sections that extend perpendicular and parallel to the longitudinal axis of the electrical bushing. Said conducting sections are each connected to each other in a serial manner. The conducting sections providing the inductor 58 are formed by the conducting element 30 and thus include a cermet. The conducting sections extend alternately perpendicular and parallel to the longitudinal axis of the electrical bushing and thus have a longitudinal extension that includes a kink at each end of a conducting section. Since the conducting sections of the inductor 58 are connected to each other throughout and are also connected to the connection sections 54a, b, an electrically conductive connection is established between the connection section 54a and 54b as the result. The inductor provided by the conducting sections and the capacitors provided by the groups of electrodes 52a-52b' form an in-series LC anti-resonant circuit that serves as electrical filter of the filter structure.

In one embodiment that may be illustrated through FIG. 1, the electrical bushing includes electrode surfaces that extend in the form of cylinders about the longitudinal axis of the bushing. The electrode surfaces are subdivided into a first and a second group, whereby the first group of electrode surfaces is connected to a first connection section, as indicated by reference number 54a, and the second group of electrode surfaces is connected to a second connection section, as indicated by reference sign 54b. The electrode surfaces therefore extend concentric and at various radii about the longitudinal axis and, further, are alternately connected to the two connection sections 54a and 54b.

Moreover, a bushing according to one embodiment can contain the electrode surfaces 52a and 52b as well as 52a' and 52b' as optional features. The bushing can include just the pair of electrode surfaces 52a, b or just the pair of electrode surfaces 52a', b' or neither of said pairs of electrode surfaces. The bushing can include only one inductor according to one embodiment as well as further optional components. Further optional components can be provided in the form of a frequency-selective component and/or can be provided by means of electrode surfaces of the conducting element. The electrode surfaces 52a, b; 52a', b' illustrated in FIG. 1 can be oriented perpendicular to the longitudinal axis of the bushing as illustrated or can be oriented at a different angle with respect to the longitudinal axis, for example parallel to the longitudinal axis. In one embodiment, the extension of the connection sections 54a, b of the conducting element is adapted to the extension of the electrode surfaces. For example, the connection sections 54a, b of the conducting element extend perpendicular to the electrode surfaces to which they are connected.

Figure 2:
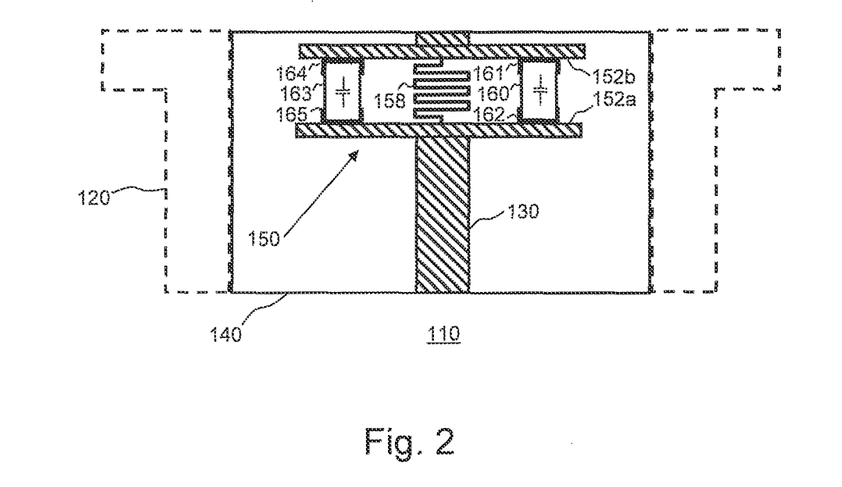
FIG. 2 illustrates a second embodiment of the electrical bushing according to one embodiment.

FIG. 2 illustrates another embodiment of the electrical bushing 110 according to one embodiment. A holding element 120 can be arranged to surround the electrical bushing, whereby the optional holding element 120 is indicated through dashed lines. The electrical bushing 110 includes a conducting element 130 and a base body 140. The conducting element 130 is arranged to be situated inside the base body. As a matter of principle, the base body can abut directly on the conducting element in order to thus form a sealing interface and/or boundary surface. The electrical bushing of FIG. 2 further includes a first connection section 152a and a second connection section 152b which each extend perpendicular to the longitudinal axis of the bushing. The connection sections 152a, b are sections of the conducting element 130.

The electrical bushing 110 further includes frequency-selective components 160, 163 in the form of SMD capacitors. The components 160 and 163 each are provided as independent bodies. The capacitors 160 and 163 border directly on the base body 130 and the conducting element, in particular on the connection sections 152a and 152b. The capacitor 160 includes two connectors 161 and 162, whereas the capacitor 163 includes two connectors 164 and 165. The capacitors 160 and 163 are aligned along the longitudinal axis of the bushing 110 and shifted radially with respect to the longitudinal axis. The connectors 161, 162, 164, and 165 each are provided through electrically conductive surfaces. The connectors 161 and 164 are electrically connected to the connection section 152b, and the connectors 162 and 165 are connected to the connection section 152a. For example, the connectors are connected to contact surfaces that are provided by the corresponding connection sections. Accordingly, the capacitors 160 and 162 are provided to be in-series in the electrically conductive connection.

The electrical bushing 110 illustrated in FIG. 2 further includes an inductor 158 which also extends between the connection sections 152a and 152b. The inductor is formed by a multitude of conducting sections of the conducting element which extend meander-shaped and for example, in accordance with the profile of a rectangular wave. The conducting sections are aligned to be alternately perpendicular and parallel to the longitudinal axis of the electrical bushing and abut on each other in 90° kinks at which the conducting sections are connected in-series to each other. The conducting sections extending parallel to the longitudinal axis, which are part of the inductor, are equal in length; likewise, the conducting sections extending perpendicular to the longitudinal axis, which are part of the inductor, are equal in length. The properties of the inductor 158 correspond to the properties of the inductor 58 in FIG. 1, and vice versa.

The bushing 110 illustrated in FIG. 2 thus includes an LC resonant circuit, whereby the inductor of the resonant circuit is provided by the inductor 158. The capacitor of the resonant circuit is provided by the parallel connection of the capacitors 160 and 163. This results in a band-stop filter that blocks frequency components near the resonance frequency of the LC resonant circuit. The blockade is attained through substantially increased attenuation of said frequency components.

The bushing 10, 110 is illustrated to have an upper side and a lower side in FIG. 1 and FIG. 2, respectively. The upper side corresponds to the upper edge, as illustrated, of the electrical bushing 10, 110, and the lower side corresponds to the lower edge, as illustrated, of the electrical bushing. Moreover, one embodiment provides an internal space of the housing of an implantable medical device to be adjacent to the lower side. Moreover, one embodiment provides the external space of the implantable medical device to be adjacent to the upper side of the electrical bushing.

In FIGS. 1 and 2, the conducting element 30, 130 is illustrated to have two end faces each, whereby one end face provides a contact surface on the lower side and one end face provides a contact surface on the upper side. In FIGS. 1 and 2, the end faces are illustrated to be flush with the upper side and/or lower side. However, at least one of the end faces can be offset in longitudinal direction of the bushing with respect to the upper side and/or lower side. The conducting element can, for example, project from the upper side and/or from the lower side such that the end face and/or the contact surface provided by it is offset towards the outside. Just as well, the conducting element can provide end faces that are offset towards the inside with respect to the upper side and/or lower side.

The components 160, 163 and the corresponding connection sections 152a, b and/or the contact surfaces provided by them each are in one embodiment optional components of the bushing. A bushing according to one embodiment can include no component, one component or more components as identified through reference numbers 160, 163 as well as the corresponding connection sections identified by reference numbers 152a, b.

FIGS. 3(a)-(e) illustrate multiple variants of circuits that can be provided by the filter structure of the bushing according to one embodiment. The variants of circuits can represent the entire filter structure or just a part thereof. For example, several of the variants of circuits illustrated in FIGS. 3(a)-(e) can be combined with each other in a bushing, in particular by serial combination of feedthrough filter circuits and/or parallel combination of dissipation filter circuits. The upper, horizontal branch of the variants of circuits illustrated in FIGS. 3(a)-(e) corresponds to the section of the conducting element that extends through the base body and/or the electrically conductive connection. The connector illustrated as a circle corresponds to a bonding to mass, for example to a connector that is connected to the housing or to a holding element.

Figure 3:
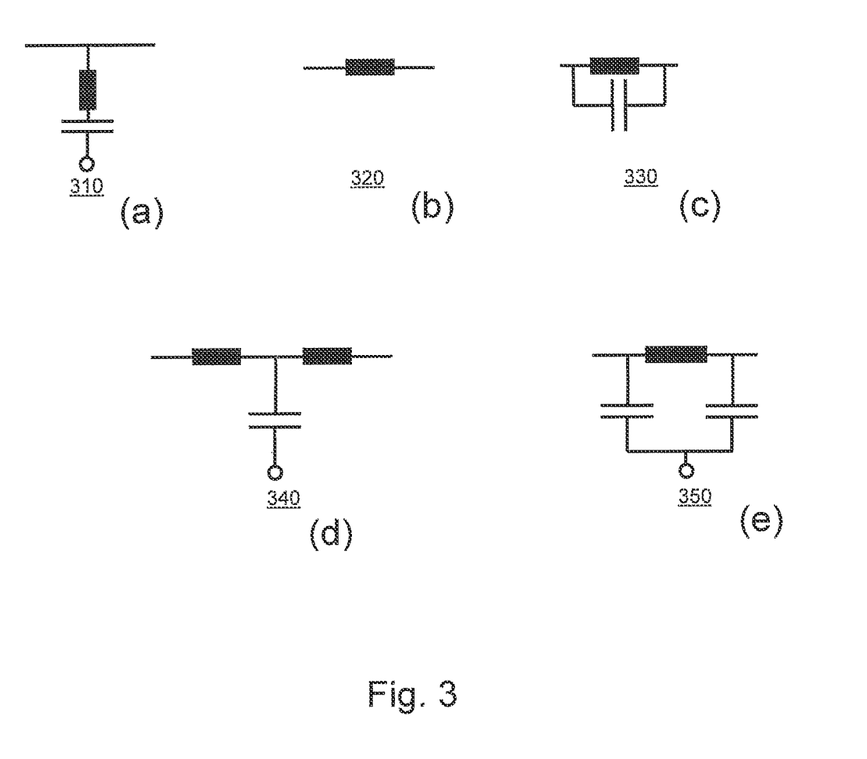
FIG. 3 illustrates multiple variants of circuits represented by the electrical filter structure of the electrical bushing according to one embodiment.

FIG. 3(a) illustrates an LC resonant circuit 310 that is connected as dissipation filter to the electrically conductive connection between the internal space and the external space. It forms a barrier for portions with a frequency near the resonance frequency and dissipates said parts to mass. FIG. 3(b) illustrates a serial filter inductor 320 in the electrically conductive connection that blocks HF portions and allows only low frequency portions to pass. FIG. 3(c) illustrates an LC anti-resonant circuit 330 that is connected in-series to the electrically conductive connection between the internal space and the external space. It forms a barrier for portions with a frequency near the resonance frequency and blocks said portions. The anti-resonant circuit 330 corresponds to the filter circuit of FIGS. 1 and 2. FIG. 3(d) illustrates a continuity filter 340 in a T-arrangement with two serial inductors and a parallel capacitor arranged in between. The parallel capacitor is connected to a tapping between the two serial inductors and to mass. This results in a second order low-pass filter. FIG. 3(e) illustrates a continuity filter 350 in a arrangement with two parallel capacitors and a serial inductor arranged in between. The serial inductor connects the capacitors, which are in a parallel arrangement, to each other, whereby the parallel capacitors each are connected between the electrically conductive connection of the conducting element and mass. This results in a second order low-pass filter. Alternatives to the variants or circuits illustrated in FIGS. 3(d) and 3(e) use parallel circuit including an inductor and a capacitor instead of the inductor, and a serial circuit including an inductor and a capacitor instead of each the capacitors. This results in higher order band-stop filters. In the variants of circuits of FIGS. 3(a)-3(c), the at least one conducting element provides at least one conducting section of the inductor of the filter structure. In the variants of circuits of FIGS. 3(a)-3(c) and in alternatives to the variants of circuits of FIGS. 3(d) and 3(e) specified above, the at least one conducting element provides at least one conducting section of at least one of the inductors of the filter structure or of all inductors of the filter structure.

The filter structure in one embodiment provides a low-pass filter or a band-stop filter providing strong attenuation of HF frequencies that are used for excitation in medical magnetic resonance imaging procedures for whole body imaging. Said HF frequencies are, for example, between 1 and 1000 MHz, for example in the ultra-short wave range from 30 to 300 MHz and/or in one embodiment at approx. B*42 MHz/Tesla, whereby B is the magnetic flux density of the static magnetic field used for magnetic resonance imaging. The value of B is assumed to be between 0.2 and 5 Tesla, in one embodiment from 1-2 Tesla. Alternatively, the value of B can be assumed to be 5-12 Tesla for modern and/or future MRI systems.

Although specific embodiments have been illustrated and described herein, it will be appreciated by those of ordinary skill in the art that a variety of alternate and/or equivalent implementations may be substituted for the specific embodiments shown and described without departing from the scope of the present invention. This application is intended to cover any adaptations or variations of the specific embodiments discussed herein. Therefore, it is intended that this invention be limited only by the claims and the equivalents thereof

What is claimed is:

1. An electrical bushing for use in a housing of an implantable medical device, the electrical bushing comprising:
    at least one electrically insulating base body comprises a ceramic; and
    at least one electrical conducting element, wherein the conducting element is set up to establish, through the base body, at least one electrically conductive connection between an internal space of the housing and an external space;
    wherein the at least one conducting element comprises at least one cermet such that the conducting element is hermetically sealed with respect to the base body; and
    an electrical filter structure, wherein the at least one conducting element provides at least a one conducting section of the filter structure and the base body provides at least one dielectric section of the filter;
    wherein the at least one electrically insulating base body and at least one conducting element are fired together thereby forming a hermetic seal therebetween, the hermetic seal consisting only of the ceramic and the cermet.

2. The electrical bushing according to claim 1, wherein the at least one conducting section is provided to have a longitudinal extension that deviates from a straight line.

3. The electrical bushing according to claim 1, wherein the at least one conducting section provides at least one part of a turn of the inductor and has an arc shape or at least one kink.

4. The electrical bushing according to claim 1, wherein the at least one conducting element provides two substantially parallel and spaced apart conducting sections of the filter structure and further provides an inductor section coupled between the two conducting sections.

5. The electrical bushing according to claim 1, whereby the conducting section comprises multiple kinks with an angle, whereby the angle between the kinks is equal and at least two angles between kinks differ in sign.

6. The electrical bushing according to claim 1, whereby the conducting element provides at least one electrode surface of a capacitor or of an electromechanical resonator that is provided by the filter structure.

7. The electrical bushing according to claim 6, whereby at least one section of the electrically insulating base body provides a dielectric layer of the capacitor or a piezoelectric body of the electromechanical resonator.

8. The electrical bushing according to claim 1, whereby the filter structure comprises an additional frequency-selective component and the conducting element provides at least one contact surface to which the additional frequency-selective component is connected, whereby the additional frequency-selective component is provided as capacitor, as additional inductor, as electromechanical resonator or as integrated filter circuit.

9. The electrical bushing according to claim 8, whereby the additional frequency-selective component comprises at least one connector that is physically connected to the at least one contact surface through a solder connection or through a press-fit.

10. The electrical bushing according to claim 1, whereby the filter structure provides the inductor formed by the conducting element as serial filter in the electrically conductive connection, or whereby the filter structure can further comprise at least one capacitor element in the form of a capacitor, whose at least one electrode surface is provided by the conducting element, or the filter structure can comprise a capacitor in the form of an additional frequency-selective component, and said capacitor element and the inductor provided by the conducting element together form an anti-resonant circuit that is arranged in-series in the electrically conductive connection.

11. The electrical bushing according to claim 1, comprising multiple conducting elements which each provide at least one conducting section of the at least one inductor of the filter structure.

12. The electrical bushing according to claim 1, whereby the filter structure and/or the at least one conducting section of the inductor provided by the conducting element is/are arranged at the surface of the bushing that is provided to border on the internal space or on the external space, or whereby the filter structure and/or the at least one conducting section of the inductor provided by the conducting element is/are arranged within the bushing.

13. The electrical bushing according to claim 1, whereby the electrical busing is configured within the implantable medical device.

14. A method for the manufacture of an electrical bushing including a filter structure for an implantable medical device, the method comprising:
    generating at least one base body green compact for at least one base body from an electrically insulating material;
    forming at least one cermet-containing conducting element green compact for at least one conducting element;
    introducing the at least one conducting element green compact into the base body green compact;
    subjecting the base body green compact with the at least one base body green compact to firing in order to obtain the at least one base body with at least one conducting element and
    forming at least one conducting section of the filter structure in the electrical bushing using the cermet-containing conducting element green compact of the at least one conducting element;

wherein forming the filter structure comprises forming an inductor provided at least in part by a section of the conducting element.

15. The method according to claim 14 further comprising providing at least one pre-made frequency-selective component into the conducting element green compact or into the base body green compact, and connecting the at least one pre-made frequency-selective component to the at least one contact surface, whereby the frequency-selective component is introduced and connected before or after the conducting element green compact is introduced into the base body green compact, or whereby the method also provides for arranging at least one pre-made frequency-selective component on or in the base body and connecting it to the conducting element after the step of firing has been carried out.

16. A method for the manufacture of an electrical bushing including a filter structure for an implantable medical device, the method comprising:

generating at least one base body green compact for at least one base body from an electrically insulating material;

forming at least one cermet-containing conducting element green compact for at least one conducting element;

introducing the at least one conducting element green compact into the base body green compact;

subjecting the base body green compact with the at least one base body green compact to firing in order to obtain the at least one base body with at least one conducting element; and forming at least one conducting section of the filter structure in the electrical bushing using the cermet-containing conducting element green compact of the at least one conducting element;

wherein forming the filter structure comprises forming a capacitor element having at least one electrode surface provided by a section of the conducting element and having a dielectric layer provided by a section of the base body.

* * * * *